(12) United States Patent
Kim

(10) Patent No.: US 7,730,629 B2
(45) Date of Patent: *Jun. 8, 2010

(54) SURGICAL DEPTH INSTRUMENT

(75) Inventor: John Y. S. Kim, Chicago, IL (US)

(73) Assignee: Eidosmed LLC, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/261,914

(22) Filed: Oct. 30, 2008

(65) Prior Publication Data

US 2009/0049705 A1 Feb. 26, 2009

Related U.S. Application Data

(63) Continuation of application No. 11/657,176, filed on Jan. 23, 2007, now Pat. No. 7,444,756, which is a continuation of application No. 11/081,147, filed on Mar. 16, 2005, now Pat. No. 7,165,336.

(51) Int. Cl.
*A61B 5/107* (2006.01)
(52) U.S. Cl. .......................................................... 33/512
(58) Field of Classification Search ............... 33/512
See application file for complete search history.

(56) References Cited

U.S. PATENT DOCUMENTS

| | | | | |
|---|---|---|---|---|
| 1,526,478 A | * | 2/1925 | Jarvis et al. | 16/38 |
| 2,920,395 A | | 1/1960 | Germann | |
| 3,916,529 A | * | 11/1975 | Mousseau | 600/547 |
| 3,943,914 A | * | 3/1976 | Grenfell et al. | 600/589 |
| 4,005,527 A | * | 2/1977 | Wilson et al. | 606/102 |
| 4,033,043 A | * | 7/1977 | Cunningham | 33/806 |
| 4,224,951 A | | 9/1980 | Hasson | |
| 4,432,376 A | * | 2/1984 | Huszar | 600/587 |
| 4,708,647 A | * | 11/1987 | Pippin et al. | 433/32 |
| 4,718,850 A | | 1/1988 | Knebelman | |
| 4,845,646 A | | 7/1989 | Marquis et al. | |
| 5,013,318 A | * | 5/1991 | Spranza, III | 606/102 |
| 5,056,238 A | | 10/1991 | Chi | |
| 5,212,871 A | * | 5/1993 | Luccarelli | 33/555.4 |
| 5,490,335 A | | 2/1996 | Chu | |
| 5,548,903 A | * | 8/1996 | Johnson et al. | 33/810 |
| 5,801,761 A | * | 9/1998 | Tibor | 348/51 |
| 5,873,175 A | | 2/1999 | Johnston | |
| 6,145,509 A | * | 11/2000 | Tanner | 128/897 |
| 6,279,248 B1 | * | 8/2001 | Walters | 33/784 |

(Continued)

FOREIGN PATENT DOCUMENTS

WO    WO 00/78258 A1    12/2000

(Continued)

*Primary Examiner*—Christopher W Fulton
(74) *Attorney, Agent, or Firm*—Drinker Biddle & Reath LLP

(57) ABSTRACT

A depth gauge for measuring the depth of a hole in a bone is disclosed having a digital readout for providing the measurement to a surgeon. The depth gauge has a probe with a tip inserted into and positioned proximate to the depth the hole, and has a reference member adjustably positioned relative the probe and against the bone proximate the hole. A measuring device is provided with the depth gauge for measuring the relative distance between the tip and the reference member, and the measuring device has a large, digital display for providing the relative distance.

12 Claims, 3 Drawing Sheets

U.S. PATENT DOCUMENTS

| | | | |
|---|---|---|---|
| 6,494,848 B1 * | 12/2002 | Sommercorn et al. | 600/587 |
| 6,508,012 B2 * | 1/2003 | Wells, Jr. | 33/784 |
| 6,665,948 B1 * | 12/2003 | Kozin et al. | 33/833 |
| 6,811,557 B2 | 11/2004 | Schraga | |
| 6,990,746 B2 | 1/2006 | Penna et al. | |
| 7,025,774 B2 | 4/2006 | Freeman et al. | |
| 7,076,886 B2 | 7/2006 | Fullerton | |
| 7,165,336 B2 * | 1/2007 | Kim | 33/512 |
| 7,444,756 B2 * | 11/2008 | Kim | 33/512 |
| 2003/0047009 A1 * | 3/2003 | Webb | 73/862.541 |
| 2003/0088991 A1 | 5/2003 | Fullerton | |
| 2005/0066535 A1 | 3/2005 | Rupp et al. | |
| 2006/0041241 A1 * | 2/2006 | Herndon | 604/500 |
| 2006/0207119 A1 | 9/2006 | Kim et al. | |
| 2006/0224161 A1 | 10/2006 | Bhattacharyya | |

FOREIGN PATENT DOCUMENTS

| | | | |
|---|---|---|---|
| WO | WO 2005/027745 A1 | 3/2005 | |

* cited by examiner

SURGICAL DEPTH INSTRUMENT

CROSS-REFERENCE TO RELATED APPLICATIONS

This patent application is a continuation of U.S. patent application Ser. No. 11/657,176, filed Jan. 23, 2007, which issued as U.S. Pat. No. 7,444,756 on Nov. 4, 2008, and which is a continuation of U.S. patent application Ser. No. 11/081,147, filed Mar. 16, 2005, which issued as U.S. Pat. No. 7,165,336 on Jan. 23, 2007, all of which are herein incorporated by reference in their entirety.

FIELD OF THE INVENTION

The invention relates to an instrument for determining the depth of a hole and, in particular, a depth gauge for providing a digital measurement of the depth of a hole in a bone.

BACKGROUND

Many surgical procedures utilize surgical devices secured to the bone of a patient. In some instances, a bone plate may be utilized that spans and secures together one or more bones or pieces thereof. In other instances, a screw or other fastener may be fastened to a bone without another device, such as a screw used to secure a transplanted tendon.

In many of these procedures, it is preferred to create a pilot hole in the bone prior to securing the fastener in the bone. Oftentimes, this preference arises from the importance of having a fastener that is inserted to a proper depth. That is, the opposite side of the bone from the drill site will typically be abutted by soft tissues that may be harmed if the screw is too long. As an example, a fastener mounted in the pedicle portion of the human spine should not extend to a point where the fastener contacts the spinal cord itself, an event that can cause irreparable nervous system damage including paralysis.

In other examples, immediate short-term damage is not a significant issue from slight over-drilling because the tissue on the opposite side will heal quickly. Over-drilling through a metacarpal may simply result in damage to the fat layer within the finger. However, if a screw is used that is too long, it may protrude and be tactilely felt by the patient, or it may pierce the skin itself. In addition, the screw may prevent soft tissues moving over the bone surface, such as tendons, ligaments, or muscles.

During drilling, the surgeon is typically capable of recognizing the resistance on the drill in order to determine when the drill has penetrated through the bone. Because the simple act of drilling does not provide an exact measurement of the depth of the bone itself, a depth gauge is commonly employed for directly measuring the depth of the hole from the top, drilling side to the bottom, opposite side.

Currently, many designs are known and utilized for measuring the depth of a hole or bore in a portion of a bone. Generally speaking, these designs utilize a central probe member having a barb at a distal end, and a sleeve or channel member. The probe member is inserted into the pilot hole while the surgeon attempts to find the surface with the barb. More specifically, the probe member is inserted to a depth greater than the depth of the pilot hole so that the barb is beyond the opposite side, at which point the surgeon finds the surface by hooking the barb to the opposite side.

The probe member is received in the sleeve or channel member and may reciprocate relative thereto. The channel member has graduated markings along a portion of its length, typically in inches and/or millimeters. A marker is laterally secured to the probe member such that, as the probe member shifts relative to the channel member, the marker indicates the relative shift between the probe member and the channel member. Accordingly, once the probe member has been secured to the opposite side of the bone, the channel member is shifted relative to the probe member and toward the bone until the channel member abuts the surface of the bone. The depth gauge is then read by examining graduated markings indicated by the probe member marker.

A number of problems are experienced with this depth gauge. As an initial point, the components are typically made with surgical-grade stainless steel, and the graduated markings are embossed therein. Therefore, the brightness of the operating room lights on the highly reflective surface can make the markings difficult to read. The markings are commonly in small increments, such as millimeters, and surgeons often have trouble differentiating between the markings, or noting partial increments. Reading these gauges, then, often requires carefully holding the depth gauge as the reading is taken, and a surgeon's effort to closely examine the reading may result in a loss of securement or purchase of the barb on the bone, thus necessitating a re-measurement and a loss of time.

Proper reading of the markings requires a surgeon's eyes to be properly aligned with the markings. That is, a proper view of the measurement requires the surgeon to view the gauge from a lateral point of view so that the view of the probe marker aligned with the graduated markings is proper not distorted by the surgeon's elevated, standing perspective. Therefore, it is often necessary for the surgeon to bend over while using these gauges to view an accurate reading. If the depth gauge is tilted in order to make the reading, the sleeve will shift relative to the probe, thus making the measurement inaccurate and possibly causing the barb to become unsecured, as discussed above.

In addition, removing of the depth gauge often causes the measurement to be lost. As the bone is essentially clamped, by light pressure, between the distal end of the channel member and the distal barb of the probe member, it is often necessary to retract the channel member from the bone surface in order to extract the probe from the pilot hole.

Additionally, if such retraction were not necessary, it is still difficult to extract the barb of the probe member without altering the measurement reading. Because the pilot hole has a relatively small diameter, and the probe member is relatively deflectable, a small amount of manipulation is required to remove the probe member. When this manipulation is through cancellous bone, the barb may become snagged while being extracted. These issues are compounded by the fact that the surgical procedure often requires multiple screws, and surgeons prefer to move quickly by taking their measurements, selecting their screws, and securing the screws in the pilot holes, each in rapid succession. Clearly, it would be difficult and unwise to rely on a surgeon's ability to remove the depth gauge without altering the measurement provided in order to make a selection of fastener length.

Accordingly, there has been a need for an improved depth gauge for surgical procedures.

DESCRIPTION OF THE PREFERRED EMBODIMENTS

Figure 1:
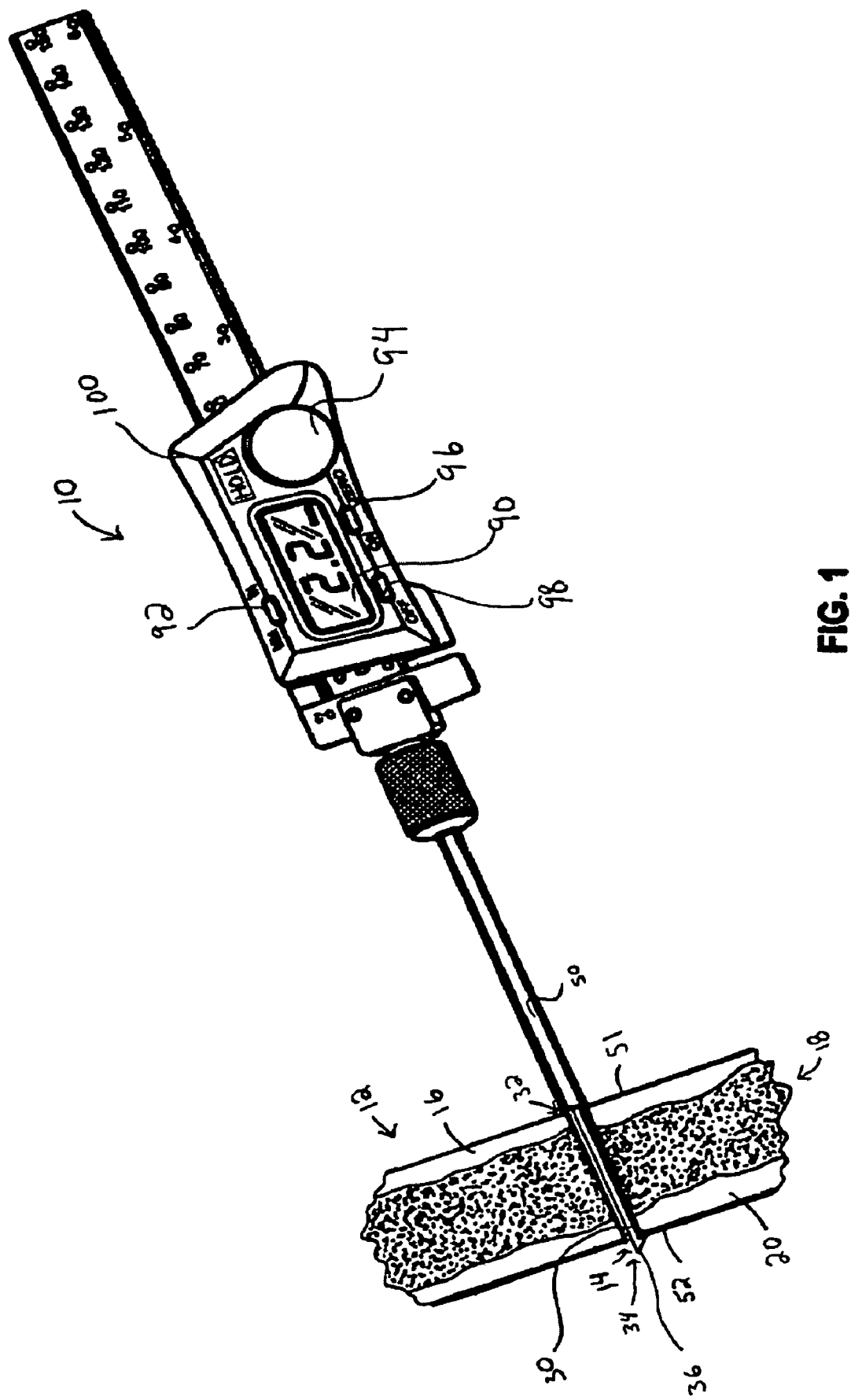
FIG. 1 is a perspective view of a form of a depth instrument of the present invention in an engaged position with a fragmentary bone portion in cross-section.
Figure 2:
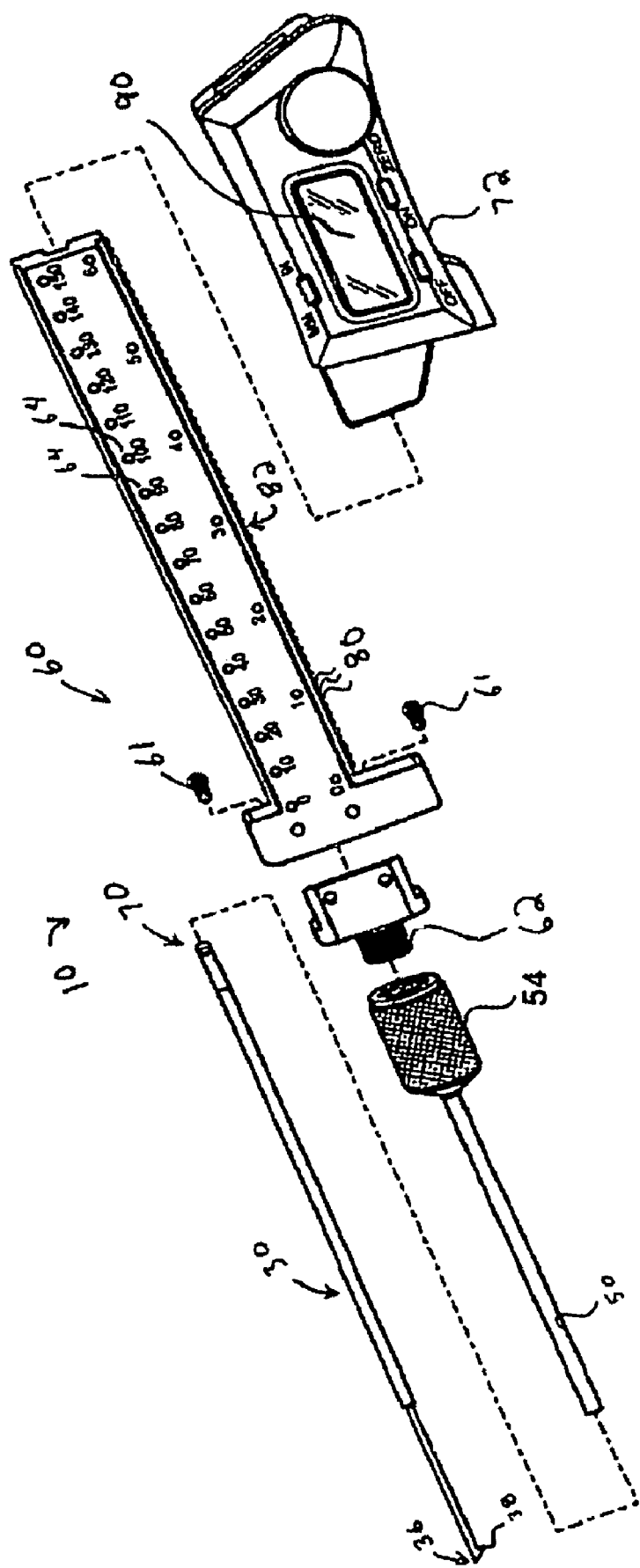
FIG. 2 is an exploded perspective view of the depth instrument.

Referring initially to FIG. 1, a depth instrument 10 is depicted secured with a bone portion 12 in order to measure the depth of a passageway in the form of a bore or hole 14 formed therein for receiving a fastener such as a screw (not shown). As can be seen, the bone portion 12 is bi-cortical. That is, the bone portion 12 has a first, proximal cortical layer 16, a cancellous layer 18, and a second, distal cortical layer 20. However, it should be noted that the instrument 10 is suitable for use with bone portions having other structures, such as those including solid cortical bone.

As described above, the hole 14 may be a pilot hole formed in the bone portion 14. In using the instrument 10 to measure the distance from a proximal surface 51 formed on the proximal cortical layer 16 to a distal surface 52 formed on the distal cortical layer 20, the instrument 10 operates such that the relative movement between two portions respectively abutting the proximal surface 51 and the distal surface 52 provides a precise measurement of the distance there between. The instrument 10 includes a probe member 30 inserted into a proximal opening 32 of the hole 14, and through the hole 14 to a distal opening 34 thereof such that a distal tip 36 of the probe 30 extends from the distal opening 34.

The probe tip 36 includes a securement or catch in the form of a hook or barb 38 for abutting the distal surface 52, as described above, the barb 38 extending to a side of the probe tip 36. Once the barb 38 has completely passed through the distal opening 34, the instrument is shifted slightly in the direction that the barb 38 extends. A slight retraction of the probe 30 from the hole 14 allows the barb 38 to engage with the distal surface 52 of the distal cortical layer 20 so that an interference therewith is created. In this manner, the barb 38 and probe 30 are relatively positioned against the bone portion 12 and, through the use of slight tension, are retained thereon.

The instrument 10 further includes a reference portion for abutting the proximal surface 51, the reference portion being in the form of a sleeve member 50. The sleeve member 50, as depicted, is a generally hollow cylindrical member with the probe 30 received in a reciprocating fashion within the sleeve member 50. The sleeve member 50 and probe 30 are concentrically arranged so that the sleeve member 50 abuts the proximal surface 51 in a manner similar to that of a bone plate or fastener head, for instance. Accordingly, the sleeve member 50 and barb 38 cooperate such that their relative position (and therefore distance) provides an accurate measurement of the depth of the hole 14 such that a screw or fastener may be selected whose length is accommodated by the hole 14 as desired by the surgeon.

Once the barb 38 is positioned on the distal surface 52, the sleeve 50 is moved towards the proximal surface 51 such that the sleeve 50 abuts thereagainst. The sleeve 50 is secured with or integrally formed with an instrument body 60. In the present form, the sleeve 50 is secured first to a knurled collar nut 54 that is received around a threaded nipple 62. The threaded nipple 62 is secured via a pair of screws 61 to the body 60. Although the body 60 is depicted with graduated markings 64, the markings 64 are unnecessary to the preferred operation of the instrument 10.

Figure 3:
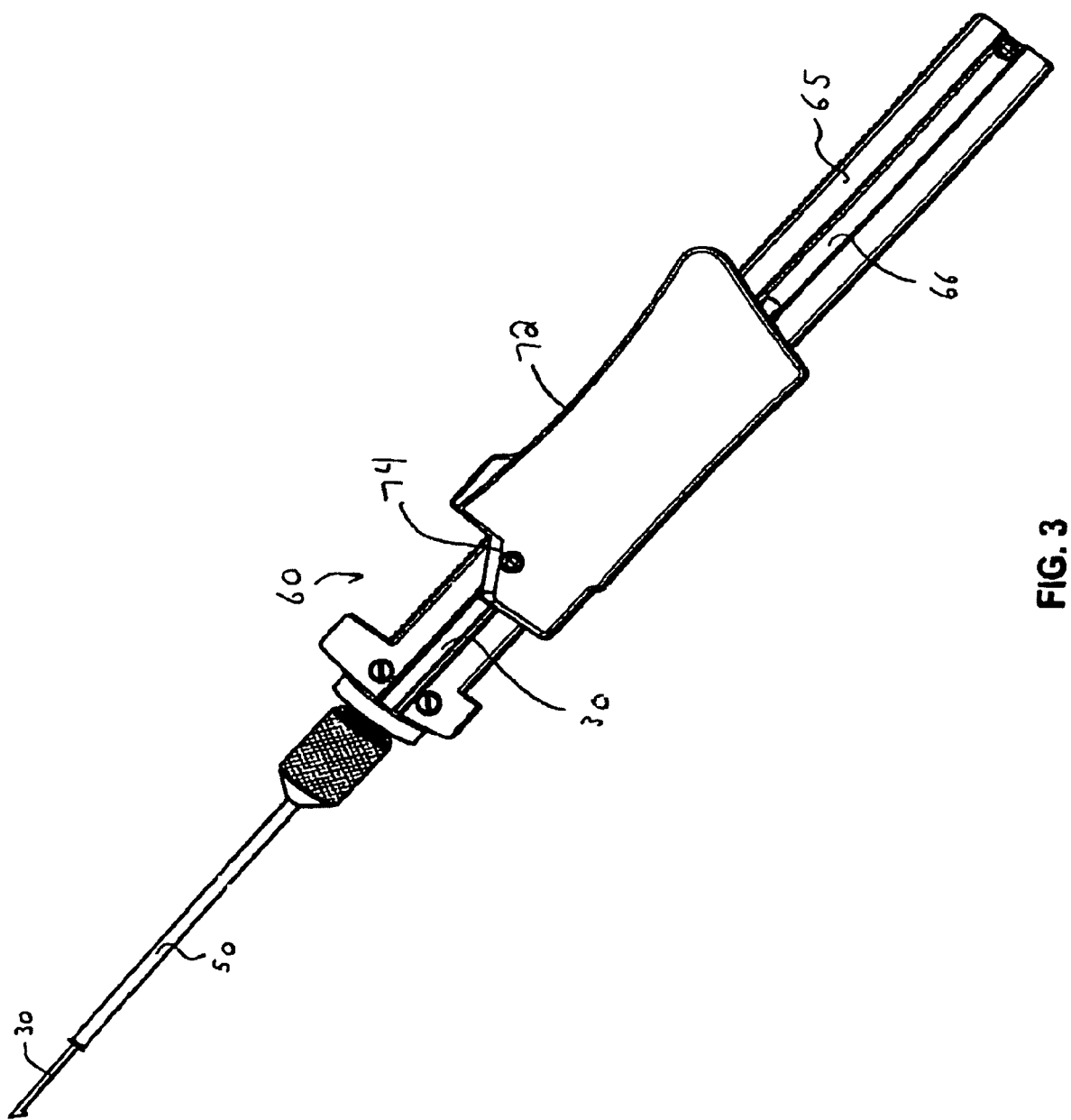
FIG. 3 is a rear perspective view of the depth instrument.

With reference to FIG. 3, the body 60 includes a rear side 65 having a channel 66 formed therein. The channel 66 is aligned with the inner cavity of the sleeve 50 such that the probe 30 extends through the sleeve 50 and into the channel 66. A proximal end 70 of the probe 30 is secured to a measuring member in the form of a slide member 72. In the presently depicted form, the probe proximal end 70 is secured to the slide member 72 with a set screw 74. The set screw 74 may be removed to allow the instrument to be dismantled, such as for removal of tissue and/or autoclaving. In addition, a quick-release connection such as a snapping collar (not shown) may be provided on either the probe 30 or the slide 72 providing a releasable connection therebetween.

The slide 72 is secured to the body 60 such that the slide 72 and probe 30 may reciprocate relative to the body 60. In this manner, when the barb 38 is secured on the distal surface 52, the slide 72 remains stationary as the sleeve 50 and body 60 are moved toward and against the proximal surface 51.

The body 60 includes teeth 80 along one edge 82 thereof. The teeth 80 cooperate with the slide 72 to provide a measurement of the movement between the slide 72 and the body 60. By way of example, such cooperation between the body 60 and slide 72 is utilized in digital calipers, such as that made by Mitutoyo America Corporation, 965 Corporate Blvd., Aurora, Ill., and by Guilin Measuring and Cutting Works, 106 Chongxin Road, Guangxi, Guilin 541002, Peoples Republic of China.

The slide 72 includes a microprocessor (not shown), or the like, and a digital electronic display 90 such as a liquid crystal display or light-emitting diode display. As the slide 72 moves relative to the body 60, the display 90 presents the measured relative motion therebetween. As can be seen, the display 90 may provide the measurement in inches, or millimeters, as selected by button 92. As the display 90 operates with electricity, a cover 94 is provided for accessing a battery compartment. The display 90 automatically returns to a "0" reading when turned on or when an "ON" button 96 is pushed. Power is shut off when an "OFF" button 98 is pushed. Furthermore, so that the reading is not lost during extraction, a "HOLD" button 100 is provided.

As can be seen, the display 90 has a large screen 102 presenting large numerals 104 that indicate a measurement between the proximal and distal surfaces 51, 52. Accordingly, the display 90 can easily be read by a surgeon. Furthermore, a surgeon may position the instrument 10 in the hole 14 for taking a measurement, depress the "HOLD" button 100 to temporarily record the reading, remove the instrument 10 from the hole 14, and then read the screen 102 on the removed instrument 10.

It should be noted that the display screen 102 may provide information other than the dimensional measurement. For instance, a particular manufacturer of surgical devices may provide the instrument 10 as part of a kit (not shown) including a bone plate that mates with a head and shank formed on a screw. The slide 72 may be calibrated to compensate for a portion of the screw head and shank received within the bone plate. Accordingly, the screen 102 may suggest a proper screw for use with the bone plate. The display 90 may also provide an indication that the reading is not stable because the sleeve 50 and probe 30 are not generally stationary relative to each other, such as in the event that compressible soft tissue is caught on the barb 38 or between the sleeve 50 and the proximal surface 51, or in the event the barb 38 is not securely positioned.

It should be noted that the instrument probe 30 may be provided without the barb 38. As an example, the probe tip 36 may be inserted to a depth such that the tip 36 is coincident with, but generally does not extend through, the distal opening 34 of the hole 14. For instance, a surgeon may place a stop or finger on the distal surface 52 of the bone 14 to recognize with the probe 30 has reached the distal opening.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

What is claimed is:

1. An electronic instrument for measuring the depth of a bore, the instrument comprising:
   a first portion including:
   a first measuring member with a generally rectangular parallelepiped shaped body defining a lengthwise axis, and
   a generally cylindrical hollow sleeve extending coaxially along the lengthwise axis from an end of the body; and
   a second portion including:
   a second measuring member that couples with the first measuring member for sliding movement along the lengthwise axis, and
   a probe extending from an end of the second measuring member and including a distal tip having a catch, the probe being disposed in the sleeve for telescoping movement along the lengthwise axis when the second measuring member is coupled with the first measuring member,
   the second measuring member and the first measuring member cooperating to generate an electrical signal according to relative movement between the first and second measuring members, the electrical signal relating to a distance between the catch and a tip of the sleeve;
   wherein the second portion further comprises a display which receives the electrical signal generated by the first and second measuring members and displays information relating to the distance between the tip of the sleeve and the catch.

2. The electronic instrument of claim 1 wherein the display is an electronic digital display.

3. The electronic instrument of claim 2 wherein the electronic digital display is a liquid crystal display.

4. The electronic instrument of claim 2 wherein the electronic digital display displays a numerical representation of the distance between the tip of the sleeve and the catch.

5. The electronic instrument of claim 1 wherein a diameter of the probe at the catch is smaller than a diameter of the bore.

6. The electronic instrument of claim 1 wherein the electronic digital display displays information relating to a fastener to be secured within the bore.

7. The electronic instrument of claim 1 wherein the generally rectangular parallelepiped shaped body further comprises a scale of graduated markings.

8. The electronic instrument of claim 1 wherein the second measuring member comprises a controller that generates the electronic signal and communicates the electronic signal to a display for displaying indicia according to the distance between the catch and a tip of the sleeve.

9. The electronic instrument of claim 1, wherein the probe can move linearly and move in an overlapping manner with the first measuring member.

10. The electronic instrument of claim 1, wherein the first measuring member comprises a channel and the probe is designed to move linearly within the channel.

11. The electronic instrument of claim 1, wherein the second measuring member surrounds, on at least three sides, the first measuring member.

12. An electronic instrument for measuring the depth of a bore, the instrument comprising:
   a first portion including:
   a first measuring member with a generally rectangular parallelepiped-shaped body defining a lengthwise axis, and
   a generally cylindrical hollow sleeve affixed coaxially along the lengthwise axis from an end of the body; and
   a second portion including:
   a second measuring member that couples with the first measuring member for sliding movement along the lengthwise axis, the second measuring member having a generally rectangular parallelepiped-shaped body, and
   a probe extending from an end of the second measuring member and including a distal tip having a catch, the probe being disposed in the sleeve for telescoping movement along the lengthwise axis when the second measuring member is coupled with the first measuring member,
   the second measuring member and the first measuring member cooperating to generate an electrical signal according to relative movement between the first and second measuring members, the electrical signal relating to a distance between the catch and a tip of the sleeve;
   wherein the second portion further comprises a display which receives the electrical signal generated by the first and second measuring members and displays information relating to the distance between the tip of the sleeve and the catch.

* * * * *